(12) United States Patent
Keranen (10) Patent No.: US 8,363,903 B2
(45) Date of Patent: Jan. 29, 2013

(54) METHOD AND APPARATUS FOR DETERMINING THE TOPOGRAPHY AND OPTICAL PROPERTIES OF A MOVING SURFACE

(75) Inventor: Heimo Keranen, Espoo (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 1104 days.

(21) Appl. No.: 12/276,215

(22) Filed: Nov. 21, 2008

(65) Prior Publication Data

US 2009/0135434 A1 May 28, 2009

(30) Foreign Application Priority Data

Nov. 22, 2007 (FI) ..................................... 20075829

(51) Int. Cl.
*G06T 7/00* (2006.01)
*G01B 11/30* (2006.01)
(52) U.S. Cl. ......... 382/108; 382/291; 356/600; 356/601
(58) Field of Classification Search .................. 382/108, 382/291; 356/600–613
See application file for complete search history.

(56) References Cited

U.S. PATENT DOCUMENTS

| | | | | |
|---|---|---|---|---|
| 4,634,279 A | * | 1/1987 | Ross et al. | 356/610 |
| 6,075,605 A | * | 6/2000 | Futamura et al. | 356/608 |
| 6,496,270 B1 | * | 12/2002 | Kelley et al. | 356/602 |
| 6,501,554 B1 | * | 12/2002 | Hackney et al. | 356/601 |
| 7,440,590 B1 | * | 10/2008 | Hassebrook et al. | 382/108 |
| 2001/0015414 A1 | | 8/2001 | Keranen et al. | |
| 2002/0039187 A1 | | 4/2002 | Keranen | |
| 2005/0219553 A1 | * | 10/2005 | Kelly et al. | 356/605 |
| 2007/0097381 A1 | * | 5/2007 | Tobiason et al. | 356/604 |

FOREIGN PATENT DOCUMENTS

| | | |
|---|---|---|
| DE | 100 63 293 A1 | 7/2002 |
| FI | 20065570 A | 8/2007 |

* cited by examiner

*Primary Examiner* — Jon Chang
(74) *Attorney, Agent, or Firm* — Birch, Stewart, Kolasch & Birch, LLP (57) ABSTRACT

A method and apparatus for determining the topography or optical properties of a moving surface of a subject are disclosed. Taking images of the moving surface at different moment in time by aiming different illuminations at the subject. Taking images of a reference area located near the moving surface synchronously with the images of the moving surface, in such a way that, in each image of the reference area, illumination of substantially the same type is aimed at the reference area, wherein the images created of the reference area are used to position image areas corresponding to the same area of the subject in the images of the moving surface.

16 Claims, 13 Drawing Sheets

- the same area Y is imaged at three different times t1, t2, and t3
- the corresponding pixels of the images can be defined using the correlation technique, by exploiting the texture in the image
- with the aid of correlation, the alignment can be performed with the accuracy of fractions of a pixel

METHOD AND APPARATUS FOR DETERMINING THE TOPOGRAPHY AND OPTICAL PROPERTIES OF A MOVING SURFACE

TECHNICAL FIELD OF THE INVENTION

The present invention relates to a method for determining the properties of a moving surface. These properties are topography, spectral reflective properties, scattering properties, colour, and polarization properties.

The invention also relates to an apparatus intended to apply the method.

BACKGROUND OF THE INVENTION

According to the prior art, a topographical map of a surface can be measured using a camera technique, for instance, using a stereo method, with the aid of structural light, and using various phase-shift techniques. In these methods, several images are typically taken of the same surface, in such a way that the manner of illumination the surface is different in each image. When the manner of illumination is selected in a specific way, these images taken in different ways can be used as a basis to calculate the topography of the surface, as well as to compensate for the effect of some other factors, for example, the texture or colour of the surface, on the result of the calculation. In terms of the methods, it is essential that the same points on the surface can be identified from the images taken of the surface under different kinds of illumination. This is simplest when the surface does not move, so that images illuminated in different ways can be taken temporally consecutively. Similarly, the scattering properties of the surface, for example, can be measured by taking several images of the surface, in each of which images the lighting geometry is different, and by comparing these images with each other.

When the surface is moving, it is more difficult to exploit these methods. The same point on the surface cannot be imaged twice in exactly the same geometry with the measuring geometry remaining constant. One solution is to take several images of the surface simultaneously using different colours. This technique is disclosed in, for instance, EP patent EP97114590: Method and apparatus for automatic inspection of moving surfaces. The problem with colour imaging is that the colours of the surface can distort topographic and scattering property measurements based on colour measurement.

If it is wished to make the apparatus as reliable as possible, mechanical components, such as camera shutters etc., should be avoided.

BRIEF SUMMARY OF THE INVENTION

The invention is intended to eliminate the defects of the prior art described above and for this purpose create an entirely new type of method and apparatus for determining the topography and optical properties of a moving surface.

The invention is based on taking at least two images, at different moments in time, of both the moving subject and of a reference area located in its immediate vicinity, in such a way that, in both of the images taken of the subject, the subject is illuminated in different ways, for example, by illuminating the subject through patterned masks, such as a sine-patterned mask, and illuminating the reference area in the images taken of the reference area in the vicinity of the subject through an unpatterned mask. The images of the reference areas illuminated through an unpatterned mask are used to locate the position in the image-formation area of the images of the areas illuminated through the patterned masks, typically using a photocell, relative to the other images.

According to the invention, at least two images of the subject are taken in the image-formation area at different moments in time, in such a way that in each image the subject is illuminated in mutually differing ways, for example, through masks, or parts of a mask, of different types, images being taken of the reference area near to the subject, to the image-formation area, at a moment in time synchronized with the images of the subject, in such a way that the reference area is illuminated in these images mutually in essentially the same way, for example, through masks of the same type, and the images thus formed of the reference area are used to locate the corresponding pixels of the images taken of the subject.

More specifically, the method according to an aspect of the invention includes taking a first image of the subject, on an image-formation area, at a first moment in time by aiming a first type of illumination; taking a second image of the subject, on the image-formation area, at a second moment in time by aiming a second type of illumination, wherein the topography or the optical properties of the moving surface of the subject are determined on the basis of the first and second images; and taking images, on the image-formation area, of a reference area located near the moving surface synchronously with the first and second images of the subject, in such a way that, in each image of the reference area, illumination of substantially the same type is aimed at the reference area, wherein the images created of the reference area are used to position image areas corresponding to the same area of the subject in the first and second images of the subject.

The apparatus according to an aspect of the invention includes means for taking a first image of the subject, on an image-formation area, at a first moment in time by aiming a first type of illumination and a second image of the subject, on the image-formation area, at a second moment in time by aiming a second type of illumination; means for determining the topography or optical properties of the subject from the first and second images; means for taking images, on the image-formation area, of a reference area located near to the moving surface, synchronously with the first and second images of the subject, in such a way that, in each image of the reference area, illumination of substantially the same type is aimed at the reference area; and means for using the images created of the reference area to position image areas corresponding to the same area of the subject in the first and second images of the subject.

Considerable advantages are gained with the aid of the invention.

With the aid of the invention, an image of the reference area, illuminated through an unpatterned mask, can be used to locate the position in the image-formation area of an image of the area illuminated through a patterned mask, so that the pixels corresponding to the imaging subject illuminated through the mask at different imagining moments can be defined.

With the aid of this new invention, a new type of camera-based method can be created, which permits the precise topography of a surface to be measured from a very rapidly moving subject, without the texture or colour of the surface affecting the measurement result.

The invention can also be applied to the measurement of the colour, spectroscopic properties, glossiness, scattering properties, or polarization properties of a surface. These properties can be measured using the same measuring system as the topography of the surface.

The invention can be used for measuring the topography of, for instance, a paper or metal surface. Preferred embodiments of the invention can also be used to determine, for example, the height of a printed impression, or the height of a conductor on an electronic circuit board, on a rapidly moving production line.

By means of the new type of method according to the invention, it is possible to implement the accurate measurement of the topography of a surface from a rapidly moving subject. The advantages of the invention are thus:
- a simple and cheap device construction
- applicability to a surface moving at very high speeds
- the method is independent of the colour and surface texture of the surface.

The method can also be used to implement the measurement of, for instance, the colour, wavelength spectrum, or polarization properties of a moving surface.

BRIEF DESCRIPTION OF THE DRAWINGS

In the following, the invention is examined with the aid of examples and with reference to the accompanying drawings.

DETAILED DESCRIPTION OF THE INVENTION

The terminology used in the following description is used in association with reference numbers as follows:
- transparency 1,
- image sensor 10,
- imaging optics 11,
- exposure optics 12,
- light sources 15-17,
- moving surface being imaged 18,
- light sources 19-20.

In addition, the following basic definitions are used in connection with the invention:
- area, on the moving surface 18, to be imaged, the topography or optical properties of which is it wished to determine=area X,
- reference area in the vicinity of the area X being imaged=area Y,
- photocell 10=camera photosensor, on the surface of which the imaging optics form an image of the area X, or the area Y that is the subject. The photocell can be, for example, a CCD or CMOS cell, which consists of, for example, 1000×1000 pixels,
- imaging optics=the optics that form an image of the area X or the area Y, which is the subject, on the surface of the photocell of the camera,
- exposure mask=penetration or reflection-type mask illuminated by some light source, the image of which is projected by the illumination optics on the surface that is the subject,
- illumination optics=the optics that project an image of the light mask on the surface of the subject.

Figure 1:
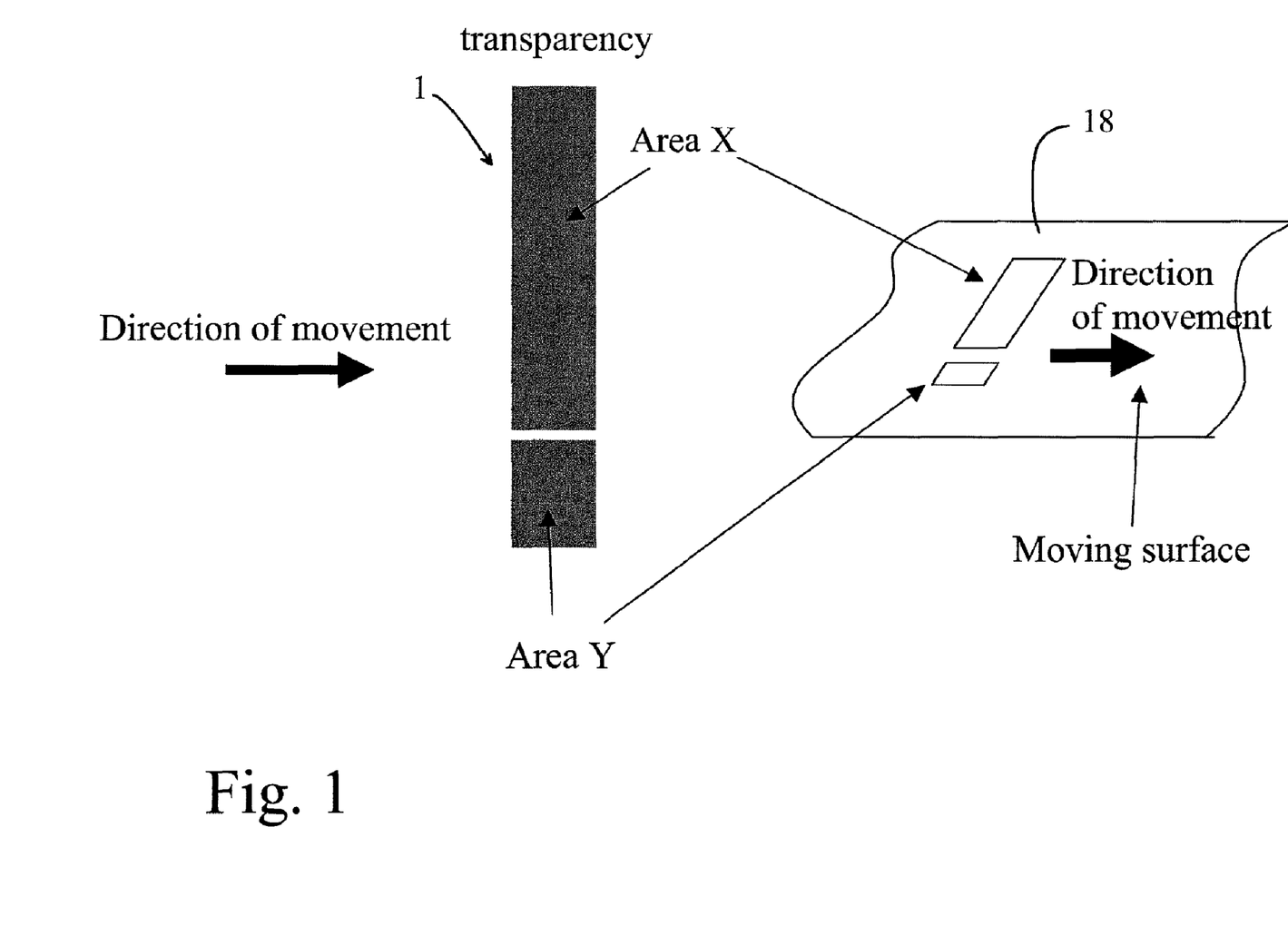
FIG. 1 shows schematically the general principle of one imaging arrangement according to the invention.

FIG. 1 shows, on a very general level, the basic solution of the invention, in which the areas X and Y are illuminated through a transparency 1, onto the moving surface 18 to be imaged.

Figure 2:
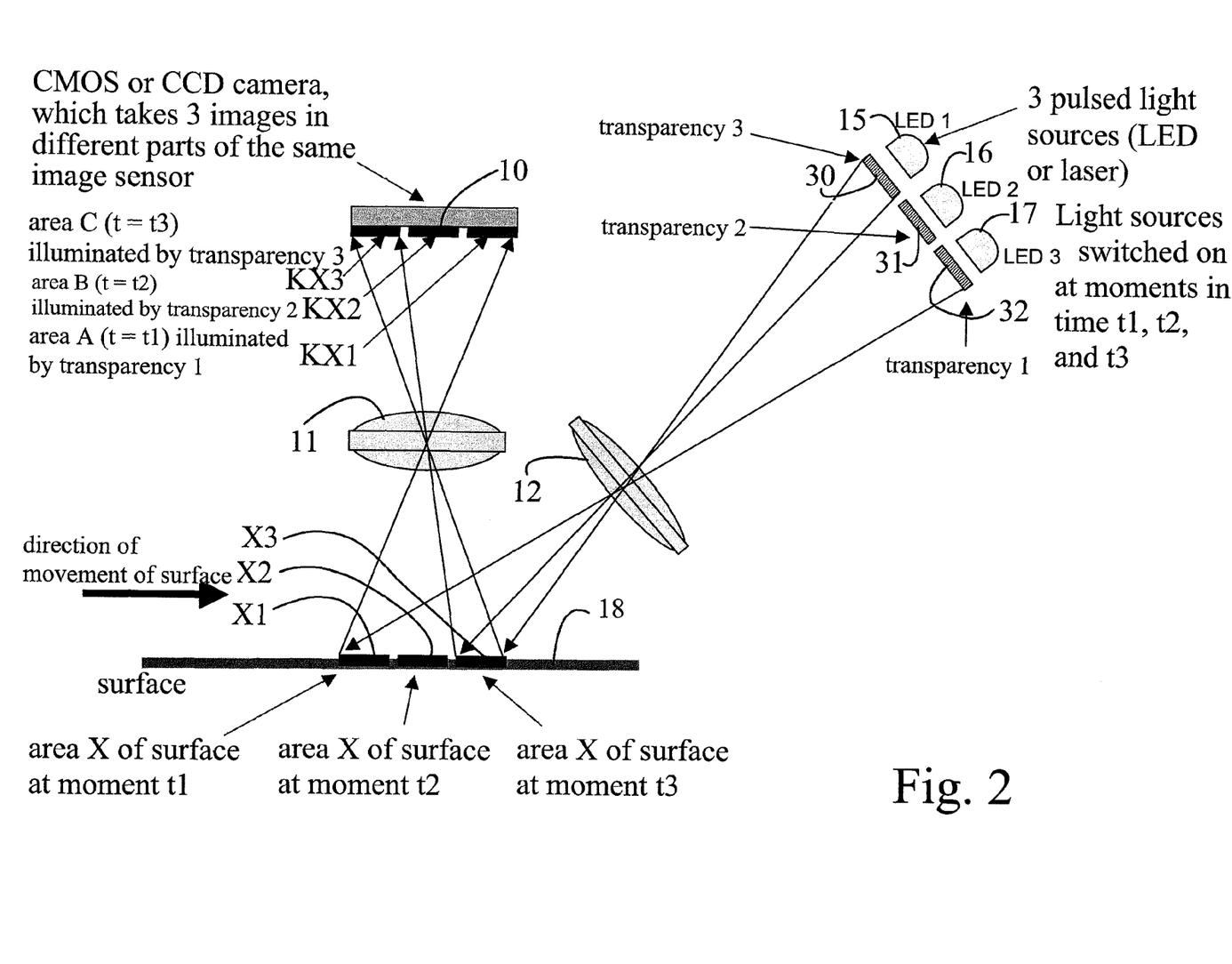
FIG. 2 shows schematically one imaging arrangement according to the invention.

FIG. 2 shows a scheme of one solution of the invention, in which the area X of the surface is imaged three times in different parts of the same image sensor, during a single camera exposure. The transparencies 30, 31, and 32 are used to project an illumination pattern of a specific type, from the light sources 15-17, onto the desired location on the moving surface 18 being imaged, through the optics 12.

Figure 3:
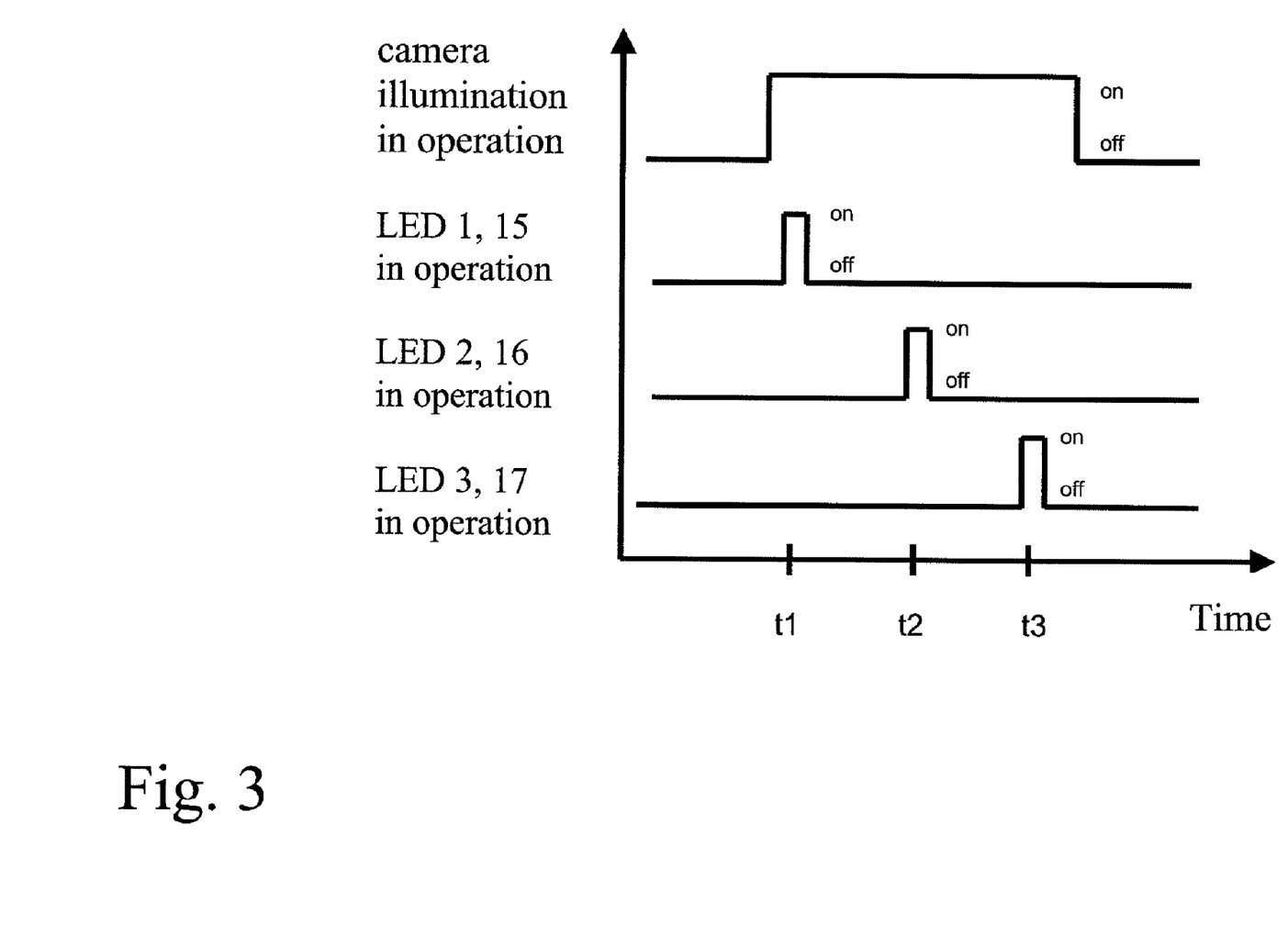
FIG. 3 shows the timing diagram of the imaging arrangement according to FIG. 2.

FIG. 3 shows the operation of the camera in connection with the light sources (LED 1-3) 15, 16, and 17. According to the figure, the exposure of the camera is continuous during the measurement, but the light sources 15, 16, and 17 are switched on at different times t1, t2, and t3. The total exposure time of the camera is thus greater than the time t1-t3. The exposure starts before the moment in time t1 and ends after the moment in time t3.

Figure 4:
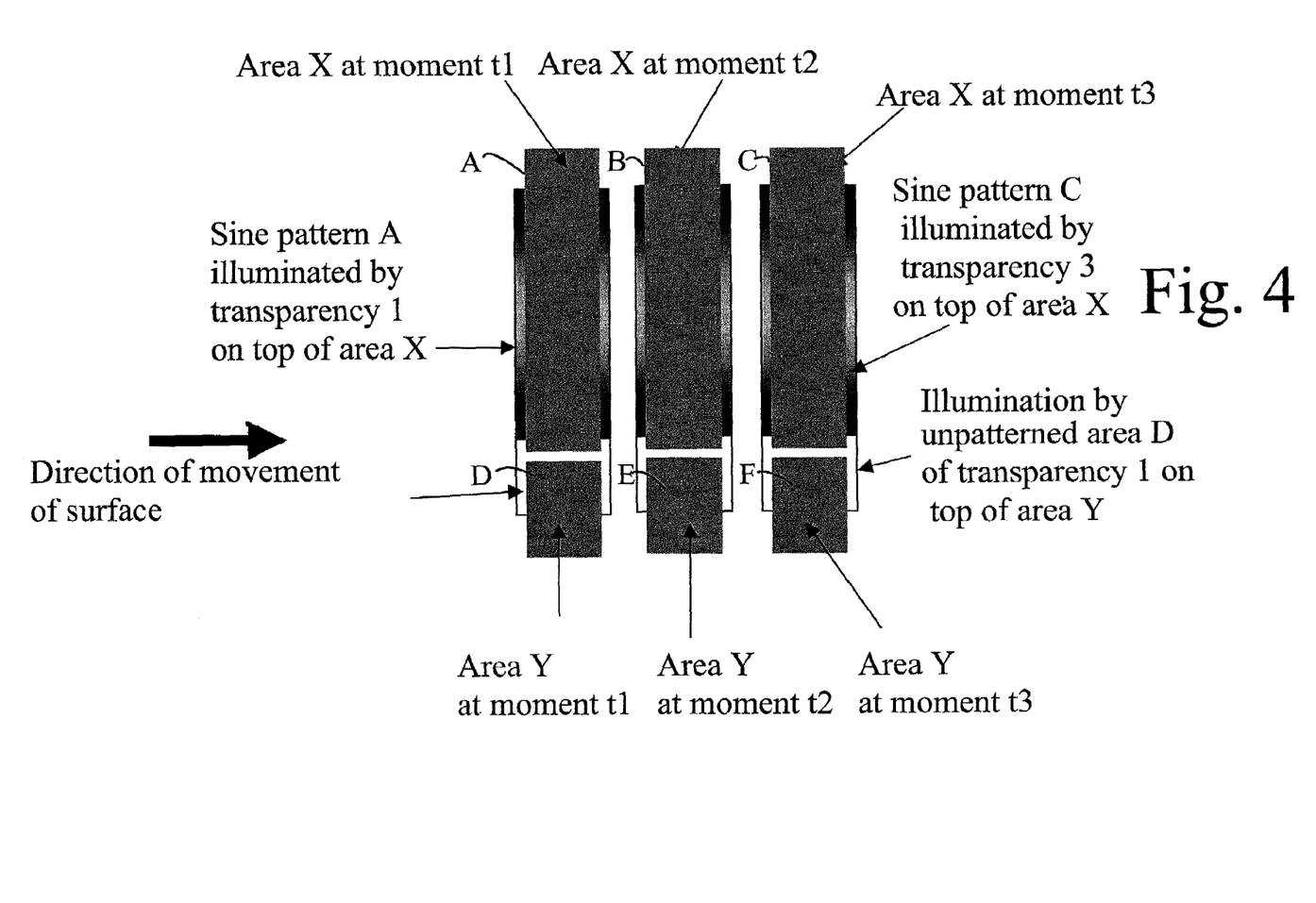
FIG. 4 shows the use in an imaging situation of transparencies used for illumination, relating to one preferred embodiment of the invention.
Figure 5:
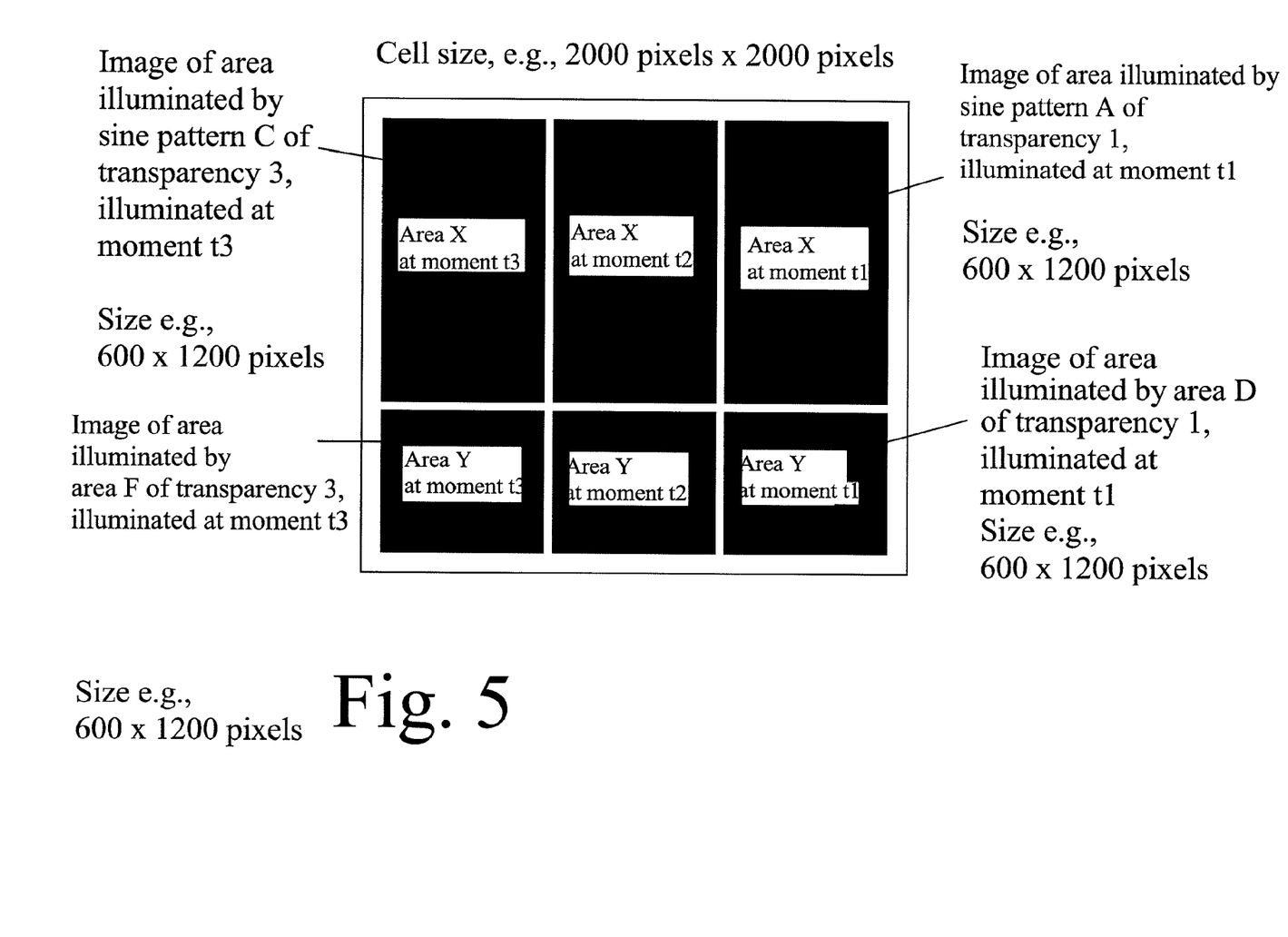
FIG. 5 shows the location in an image of areas X and Y of a surface at different moments in one solution according to the invention.
Figure 6:
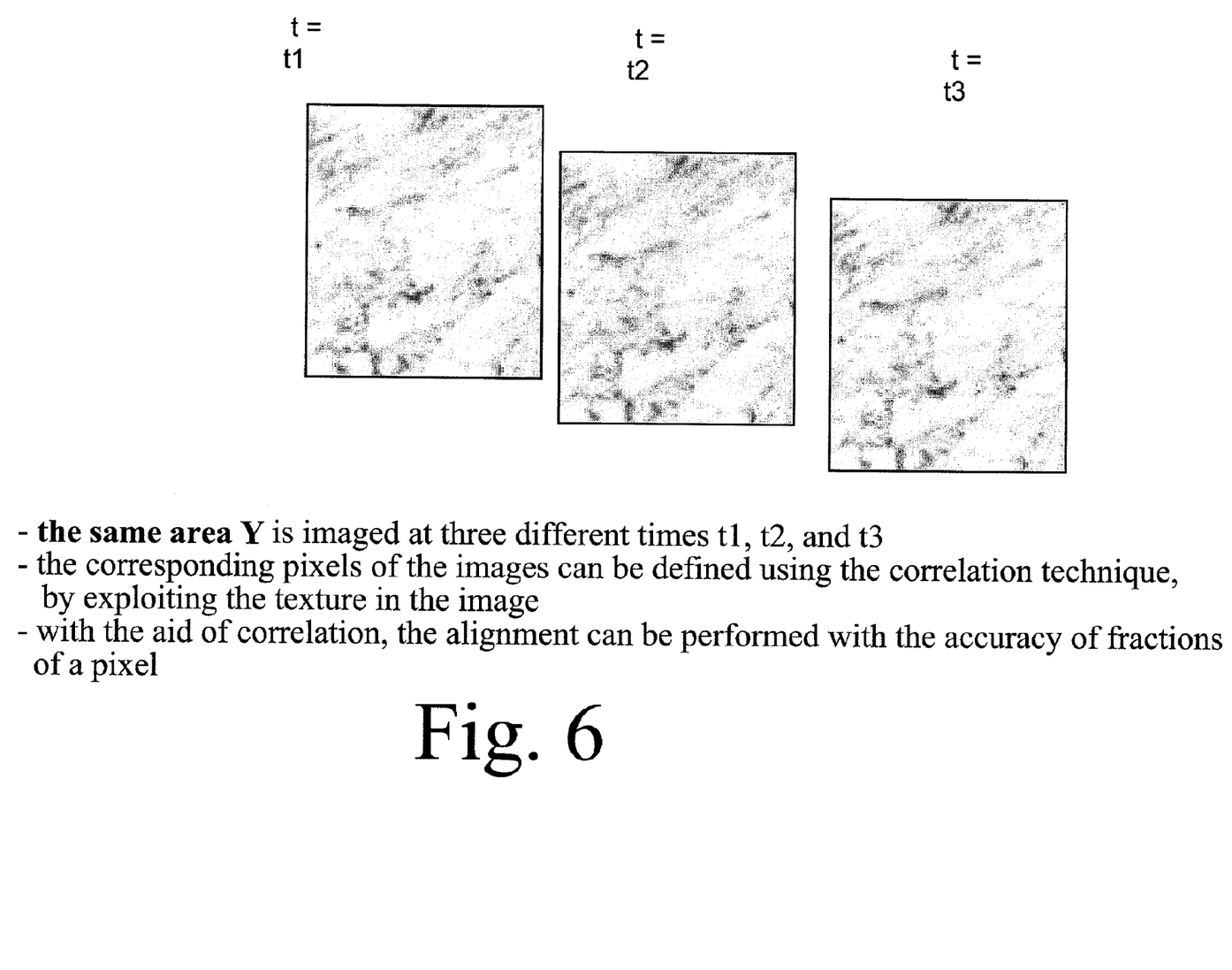
FIG. 6 shows a situation according to the invention, in which Y is imaged three times at the moments t1, t2, and t3, in different areas of the camera cell.

According to FIGS. 4, 5, and 6, three differently illuminated images A, B, and C are taken consecutively of the moving subject X, in such a way that, due to the movement, these temporally consecutively taken images are imaged through the imaging optics 11 in different areas of the camera's image sensor 10. In connection with the images A, B, and C, images D, E, and F are further taken of the area Y near to the subject X, in such a way that they have the same illumination, typically without any patterned mask.

With the aid of images D, E, and F, the corresponding pixels of area Y in each image are determined, for example, using image correlation. The term corresponding pixel refers to the image pixel corresponding to the same location in different images. With the aid of these corresponding pixels it is also possible to also define the corresponding pixels of images A, B, and C of area X, because the position of subject X relative to the reference area Y does not change in the different images. Image Y can be used to seek corresponding pixels, because the images D, E, and F taken of it are taken using the same illumination, so that the features of the surface appear the same in each image. Corresponding pixels are not necessarily found with the same accuracy in the images A, B, and C, because in each image a different sine-pattern illumination is implemented with the aid of transparencies, and covers the features of the surface differently in each image.

In this way, an image, illuminated in three different ways, of the moving subject X is obtained with the aid of the image area Y. In an ideal case, if the speed of the subject is known sufficiently accurately, the three exposure moments can be synchronized in such a way that the sine patterns of the three different images are on the surface X in a specific desired phase shift. In that case, the topography of the surface can be calculated with the aid of these three images. FIG. 7 shows the calculation formula when the phase shift of the images is precisely 120 degrees and 240 degrees between the different images. The topography can then also be calculated when the phase shift of the sine patterns is other than 120 and 240 degrees.

If the precise mutual phase shifts of the sine patterns of the images cannot be determined, for example, by timing technique, the mutual value of the phase shifts can also be determined computationally, when the corresponding pixels of the surface in the different images are known and when the illumination patterns are assumed to consist of same-phase sine patterns. Methods for this mathematical problem have been developed, for instance, Z. Wang: Advanced iterative algorithm for phase extraction of randomly phase-shifted interferograms, Optics letters, Jul. 15, 2004, Vol. 29, No. 14.

The topographic map can then be defined computationally with the aid of the mean phase-shift angles determined using the aforementioned method. The height difference of the area of the surface corresponding to the individual image pixels relative to the surrounding area then appears as a change in the phase of the sine pattern relative to the phase of the sine pattern of the environment.

When the line moves, it can be assumed that the surface 18 can also move in the vertical direction (Z direction) between an unknown number of moments in time t1, t2, and t3. This causes the same effect, as if the mean phase shift of the illumination would have changed between the moments in time. This phase shift cannot necessarily be determined precisely only from an image of the area illuminated through an unpatterned mask, if this small vertical movement does not cause changes in this image. By using the mathematical method disclosed by Z. Wang, in this case too the mean phase shift of the sine patterns can be determined and a topographic map of the surface can be calculated.

FIG. 6 shows a situation according to the invention, in which Y is imaged three times at the moments t1, t2, and t3 in different areas of the camera cell. The precise location of the surface Y between the different images, i.e. the corresponding pixels, is determined, for example, using the correlation technique. The corresponding pixels can be defined with good accuracy, because in the images taken at different times there is essentially the same type of illumination and the features of the surface appear in the same ways in the different images.

Figure 7A:
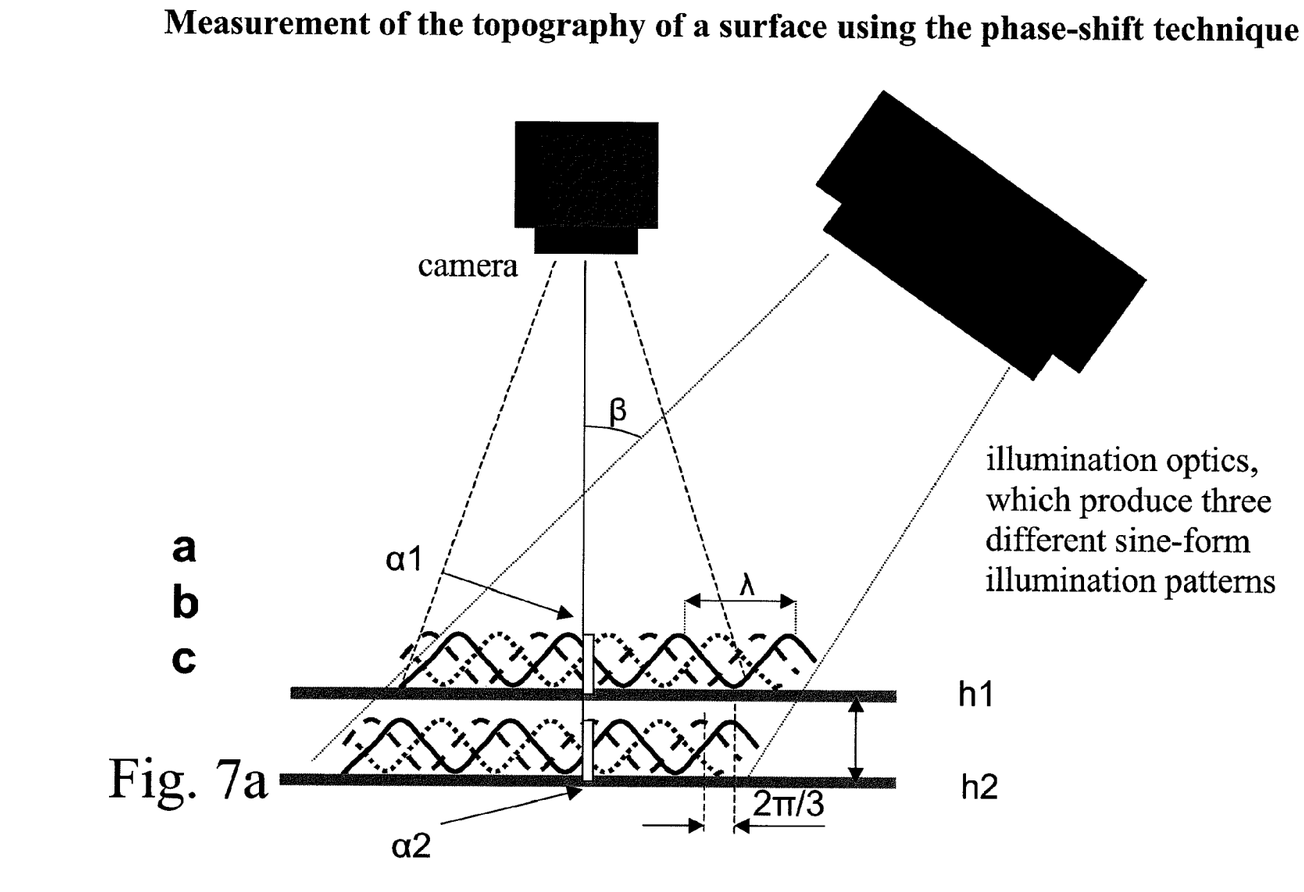
FIGS. 7a and 7b show a manner of calculating topography (Z co-ordinate) according to the invention, when there are 120-degree and 240-degree phase shifts, relative to the surface X, between three sine patterns projected on top of the surface.
Figure 7B:
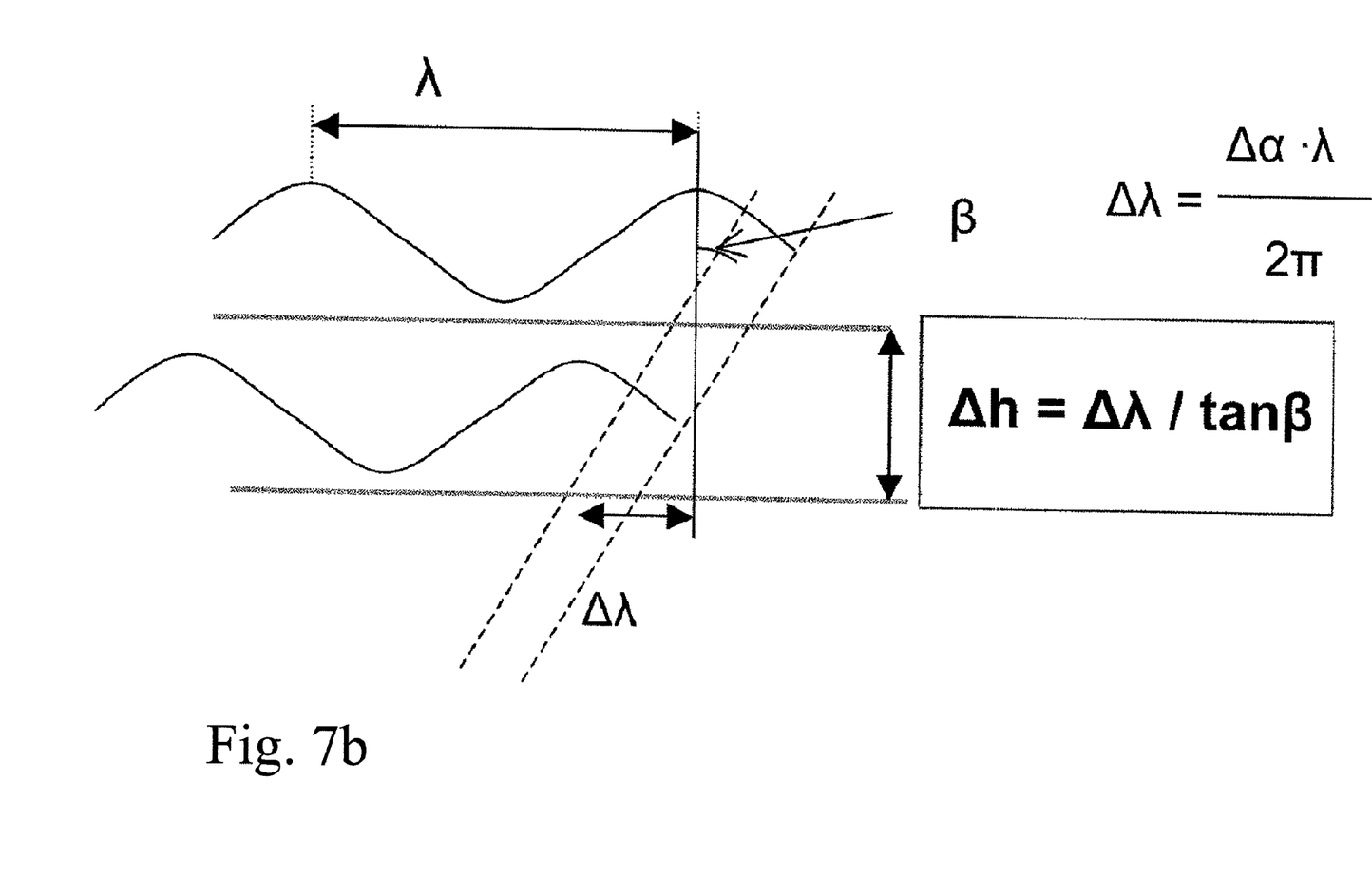

FIGS. 7a and 7b shows a method of calculating the topography (Z co-ordinate), according to the invention, when there are phase shifts, between the three sine patterns, of 120 degrees and 240 degrees relative to the surface X. In the following, the calculation of the height data from three camera images is described with the aid of the markings of FIG. 7b. The surface is illuminated at different times, by means of three different types of sine-shape illumination patterns. The phases of the sine patterns relative to each other are 0, $2\pi/3$, and $4\pi/3$. The camera then measures 3 signals a, b, and c at different moments in time, for each image point, i.e. pixel of the surface.

The equations $a = GP \sin(\alpha) + K + Z$ $b = GP \sin(\alpha + 2\pi/3) + K + Z$ $c = GP \sin(\alpha + 4\pi/3) + K + Z$ are obtained.

In these:
G=reflectivity of the surface
$\alpha$=phase of the sine pattern
P=amplitude of the sine pattern
K=signal caused by the background light
Z=offset value of the sine pattern (Z differs from zero, if the sine pattern does not have perfect contrast).

The phase angle $\alpha$ of the illumination pattern aimed at it can be solved for each image point of the surface from the equation group:

$$\alpha = \arctan\left(\frac{2a - b - c}{\sqrt{3}\,(b - c)}\right)$$

Figure 8:
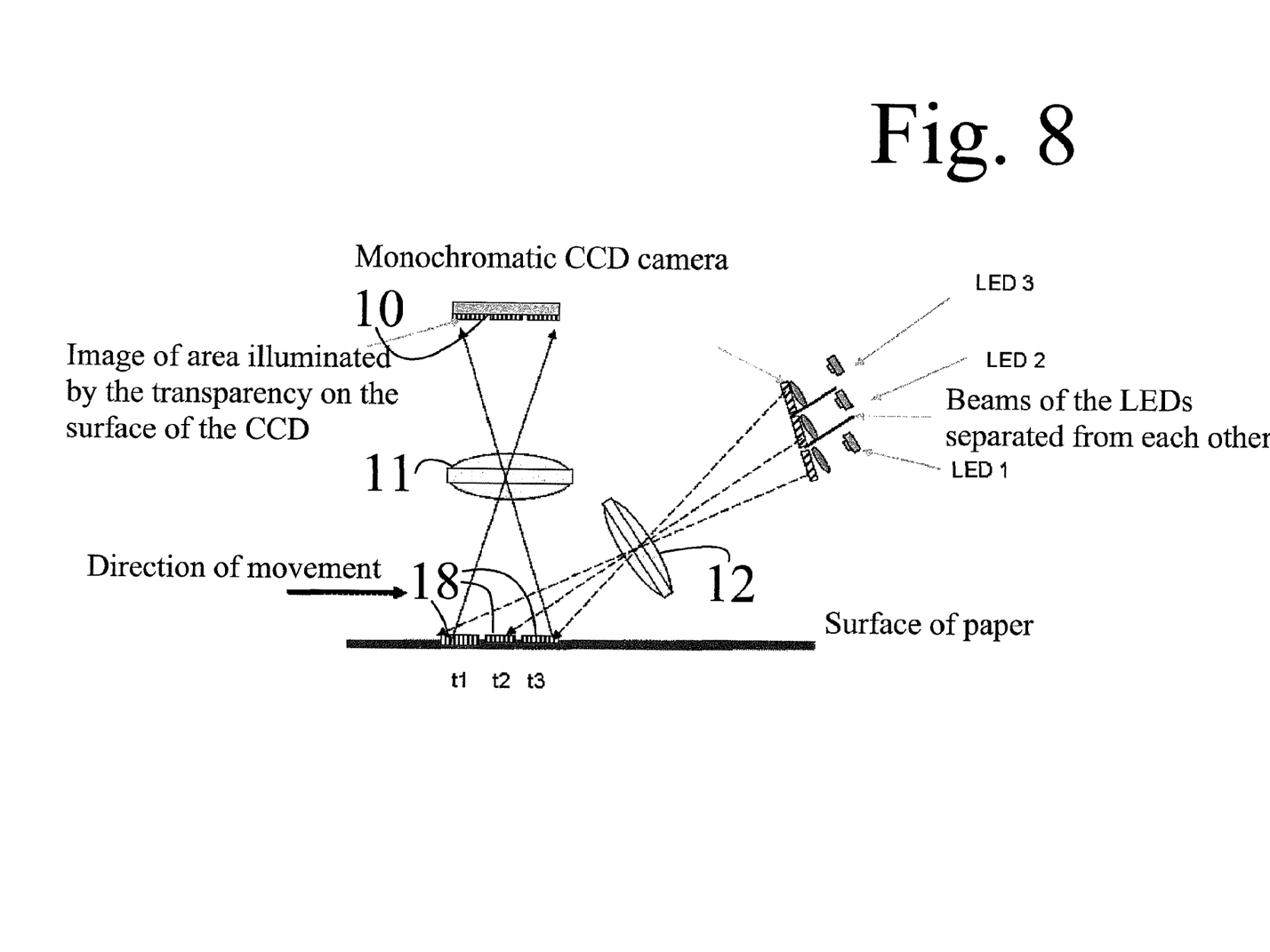
FIG. 8 shows one alternative way according to the invention to implement the measuring principle shown in FIG. 2.

The height $\Delta h$ of a point on the surface can be calculated from the phase angle $\alpha$:

$\Delta h = \Delta\lambda/\tan\tau$ in which
$\beta$=the angle of the direction of the illumination
$\lambda$=the interval length of the sine pattern
$\Delta\lambda = \alpha\lambda/(2\pi)$
$\alpha$=the phase angle of the illumination pattern FIG. 8 shows one alternative manner, according to the invention, to implement the measurement principle shown in FIG. 1, in which the beams of the light sources LED1-3 are separated from each other. The three separate transparencies are replaced with a single transparency, of which only one third is illuminated at a time, with the aid of the LEDs LED1, LED2, and LED3. The LEDs can, in principle, also be replaced with laser sources, xenon-light sources, or some other light sources that can be controlled in a pulsed manner.

Pilot tests of the method according to the invention have been made in a laboratory. In the tests, the area X was imaged three times to form a separate camera image, in such a way that in each image the surface X was located in a different place relative to the image area seen by the camera and the sine-form illumination pattern. The corresponding pixels of the images were calculated using the correlation method, with the aid of the unpatterned area Y and the height map of area X calculated with the aid of the phase shift of the sine patterns.

Figure 9:
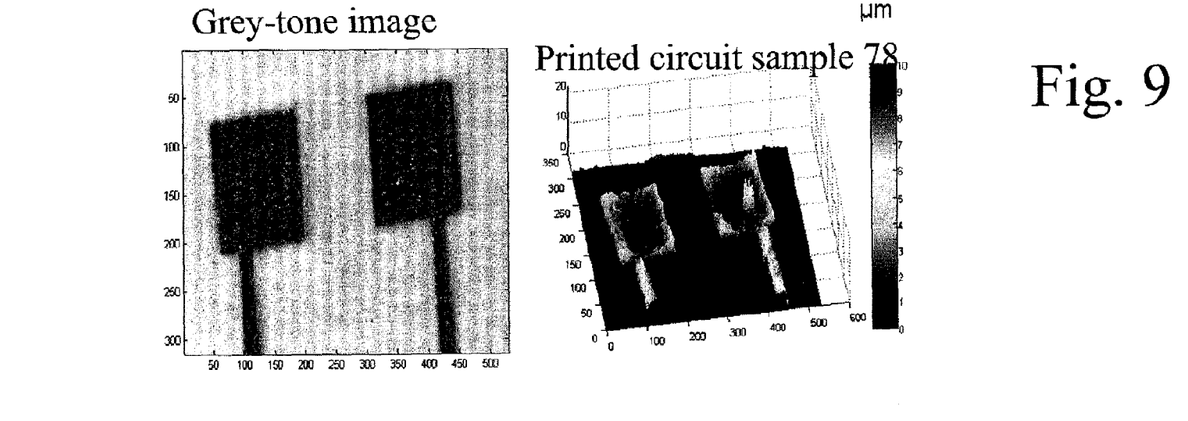
FIG. 9 shows the first results of laboratory tests relating to the testing of the functionality of the principle of the invention.

Thus, FIG. 9 shows the first laboratory test results of the invention. In the figure a) is a 2D image (sum of the sine patterns) calculated from three sine patterns, and in figure b) is a 3D map calculated with the aid of phase shift. In the figures, the pixel size is about 7 μm and the area of the image is about 4 mm×4 mm. The height of the conductor image calculated from the phase of the sine pattern is in the order of 10 μm.

Figure 10:
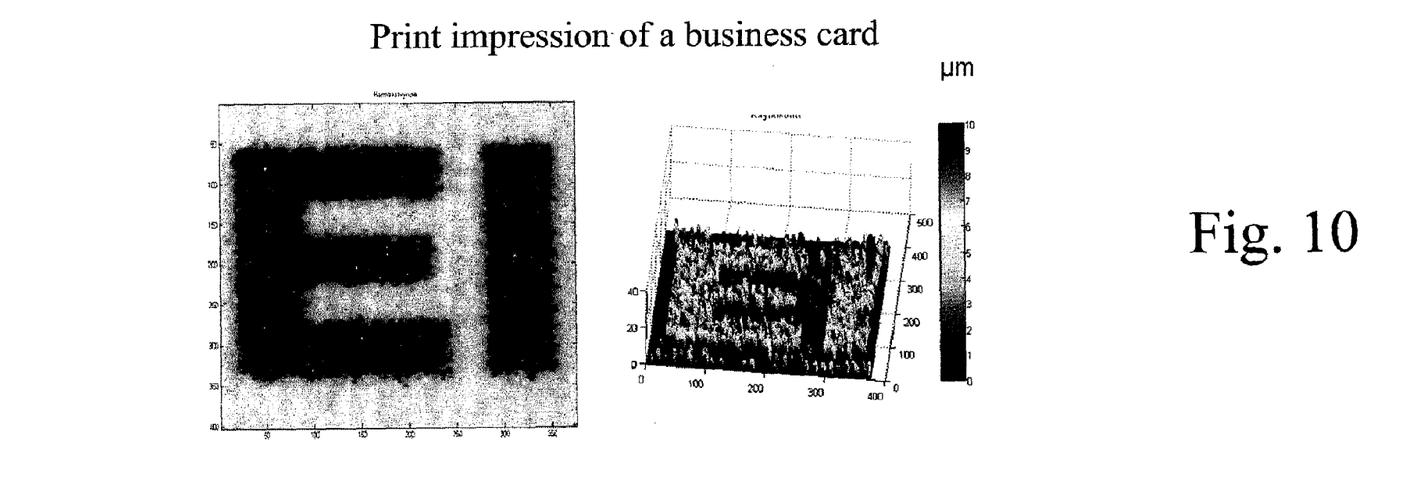
FIG. 10 shows second test results of the invention, in which a topographic map of the surface of a business card is measured in a laboratory.

FIG. 10 shows other test results of the invention, in which a topography map was measured in a laboratory from the surface of a business card. The size of the image is about 4 mm×4 mm and the height of the print impression about 10 μm.

Figure 11:
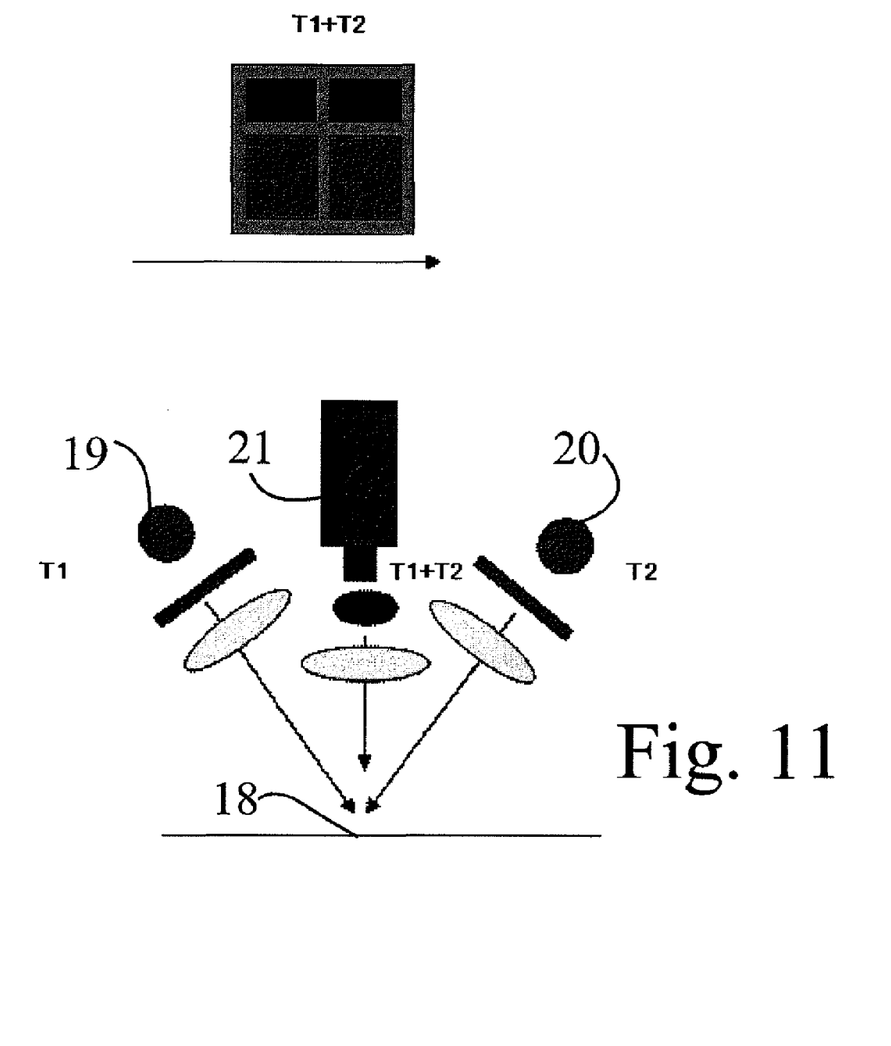
FIG. 11 shows photometric stereo imaging implemented using the method according to the invention.

By means of the method according to the invention, it is also possible to implement a high-speed measurement of a stereo image, according to FIG. 11, in which the method according to the invention is implemented by means of photometric stereo imaging. The area X is imaged from two directions being illuminated with an even lighting at the moments of time T1 and T2. The area Y is illuminated at both moments in time in the same direction. With the aid of area Y, it is possible to define the corresponding pixels of area X, after which a topography map of area X can be calculated using the principle of photometric stereo imaging.

Two light sources 19 and 20 are placed on different sides of the surface 18 being imaged and are used to illuminate, at the moments in time T1 and T2, the same area X of the surface, which is imaged using imaging optics, at the moments in time T1 and T2, in different parts of the image sensor. A third light source 21 illuminates the area Y at the same angle of illumination, at both moments in time T1 and T2. This allows the same area X to be imaged twice in different types of illumination, in such a way that the corresponding pixels of the images can be defined in the same way, with the aid of the illuminated area Y.

After this, a topographic map of the surface can be defined using the images taken from two opposite directions, with the aid of the photometric stereo method. The advantages of the method are its simple construction and the independence of the measurement from the colour of the surface, because the illumination from two directions can be made using light of the same colour.

Figure 12:
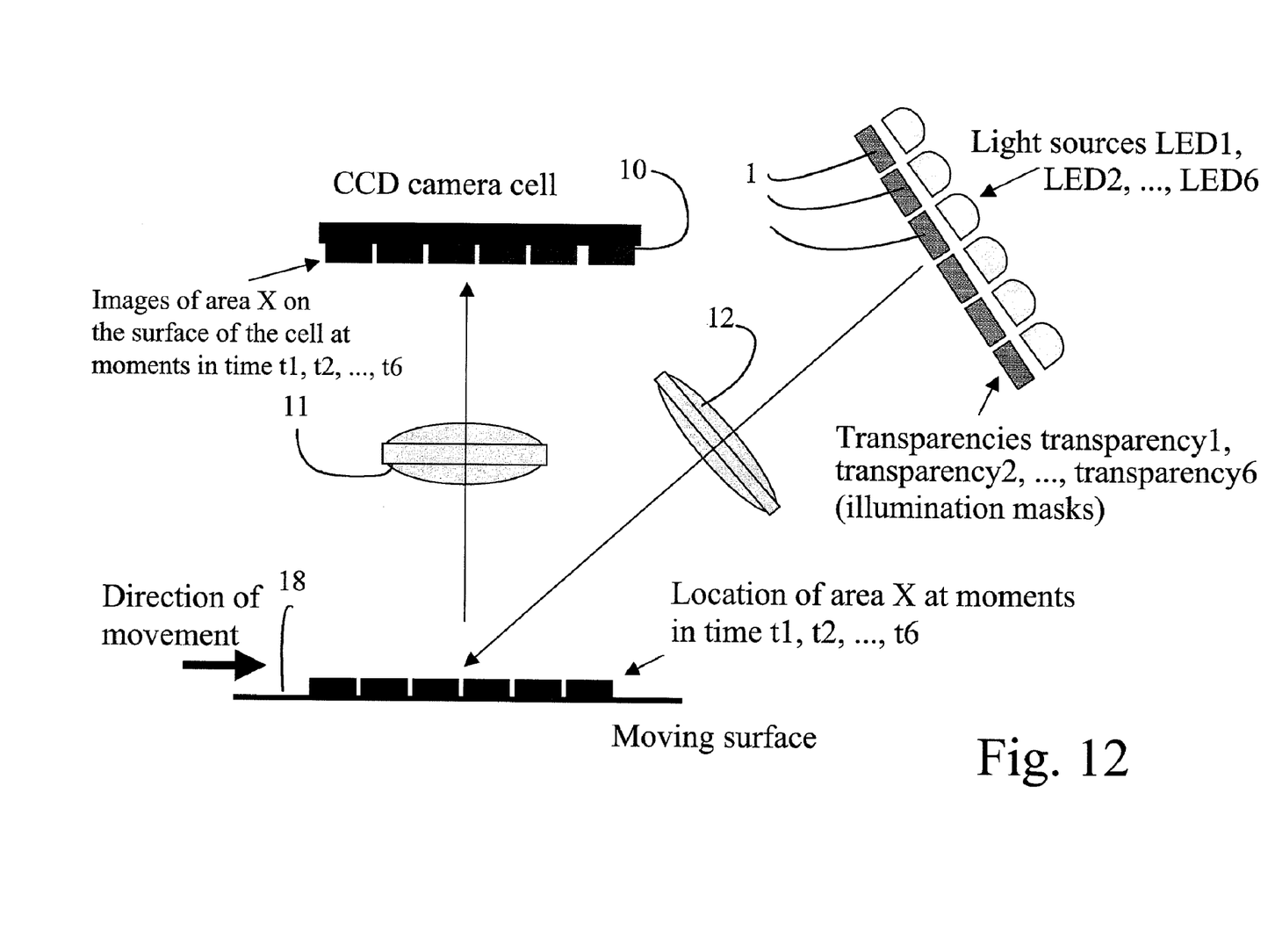
FIG. 12 shows a second alternative manner, according to the invention, to implement the measuring principle shown in FIG. 2.
Figure 13:
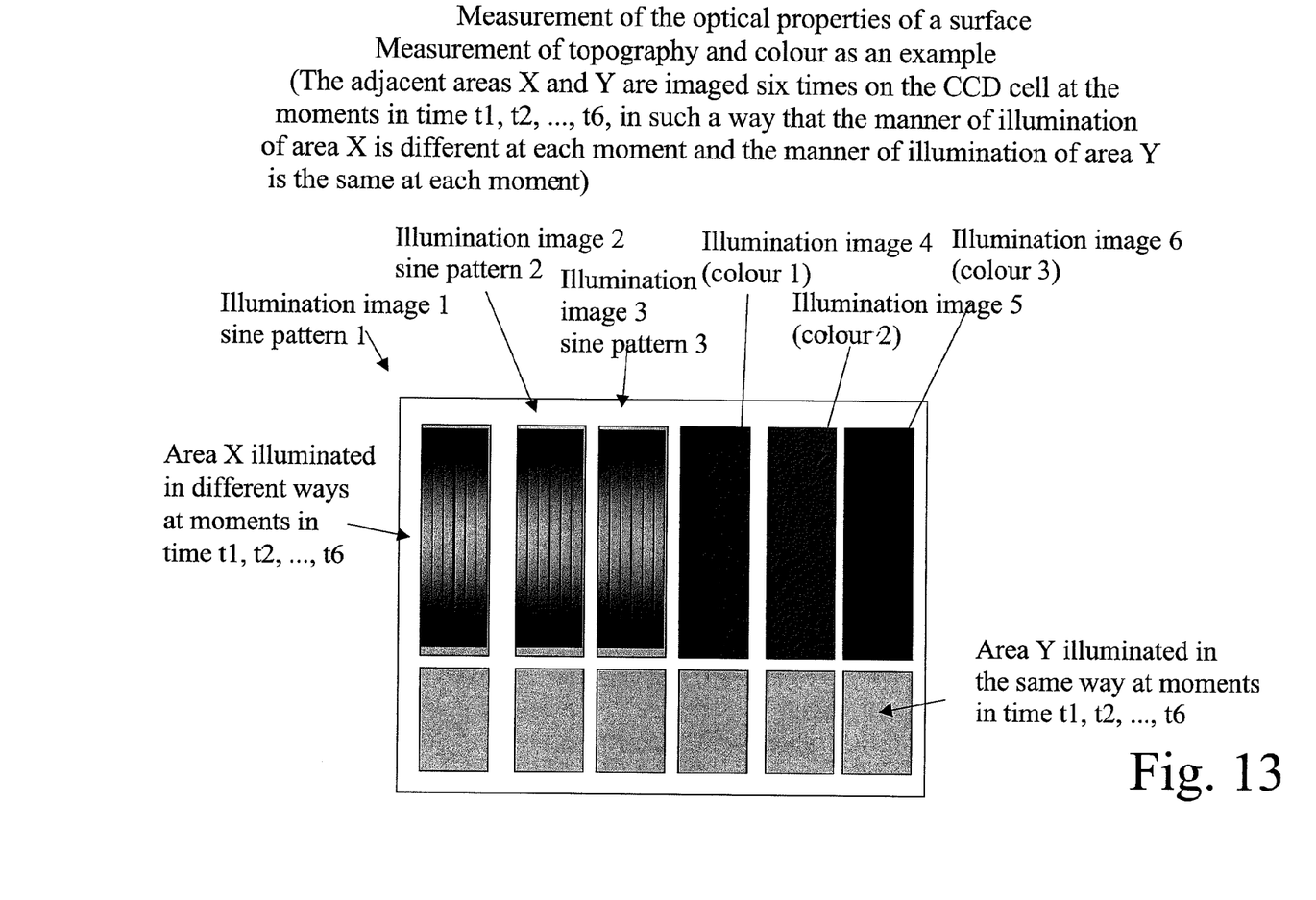
FIG. 13 shows images formed at six different moments in time, imaged in a CCD cell, using the apparatus of FIG. 12.

FIG. 12, for its part, shows an alternative solution, in which six light sources, and correspondingly six transparencies 1 are used. By means of this arrangement, an image according to FIG. 13 is created for the cell 11. Using this arrangement, the area X and the reference area Y next to it can be imaged six times at different moments in time, in such a way that in three images the area X is illuminated using different types of sine-form illumination patterns, and in three images the same area X is illuminated using coloured light, without sine-pattern masks. The reference area Y is illuminated at six different moments in time in the same way with the same colour of light.

Thus, by means of the principle according to the invention, the same arrangement can be used to measure not only the topography of the surface, but also the colour of the surface. In that case, the area X is illuminated from the same direction, but with different colours. The area Y is illuminated at all six different moments in time using the same illumination geometry and the same colour of light, so that it can be used to calculate the corresponding pixels.

By means of the method, it is possible to take two or three images, or even some other number of images. The images, illuminated in different ways, of the same subject 8 can be used, not only for measuring topography and colour, but also for other spectroscopic measurement as well as for measurement of glossiness and scattering and polarization properties of a surface, for instance. When measuring polarization properties, the images taken at different times of the area X are illuminated in different ways using polarized light. When measuring scattering properties, the images taken at different times of the area X are illuminated using light of the same colour and polarized in the same way, but from different directions. In the method, the reference area Y, illuminated in the same way, is used to synchronize these images illuminated in different ways.

The image-formation area 10 is typically a cell of one camera, but within the scope of the invention, the imaging area can also be formed of the cells of two or more cameras.

The invention claimed is:

1. A method for determining the topography or optical properties of a moving surface of a subject, the method comprising:
    acquiring a first image of an area of the subject, on an image-formation area, at a first moment in time while aiming a first type of illumination at the area of the subject;
    acquiring a second image of the area of the subject, on the image-formation area, at a second moment in time while aiming a second type of illumination at the area of the subject, wherein the topography or the optical properties of the moving surface of the subject are determined on the basis of the first and second images; and
    acquiring images, on the image-formation area, of a reference area located near the area of the subject synchronously with acquiring of the first and second images, in such a way that, in each image of the reference area, illumination of same type is aimed at the reference area, wherein the images created of the reference area are used to determine the position of image areas corresponding to the area of the subject in the first and second images.

2. The method according to claim 1, wherein the first and second images are acquired of the image areas corresponding to the area of the subject, by illuminating structural illumination patterns of different types in substantially the same direction, and the images are acquired of the reference area by illuminating with no structural illumination pattern in substantially the same direction.

3. The method according to claim 1, wherein the first and second images are acquired of the image areas corresponding to the area of the subject by illuminating light of essentially the same colour in different directions, and the images are acquired of the reference area by illuminating light of essentially the same colour in substantially the same direction.

4. The method according to claim 1, wherein the first and second images are acquired of the image areas corresponding to the area of the subject by illuminating light that is polarized in substantially differing ways, and the images are acquired of the reference area by illuminating light that is polarized in substantially the same way.

5. The method according to claim 1, wherein the first and second images are acquired of the image areas corresponding to the area of the subject are by illuminating light of spectrally different types, and the images are acquired of the reference area by illuminating light of spectrally the same type.

6. The method according to claim 1, wherein, the first and second images are acquired of the image areas corresponding to the area of the subject by illuminating sine-form illumination patterns in a different phase in substantially the same direction, and the images are acquired of the reference area by illuminating with no structural illumination pattern.

7. The method according to claim 1, wherein a single unified imaging cell is used as the image-formation area.

8. The method according to claim 1, wherein a cell structure formed of several separate cameras is used as the image-formation area.

9. An apparatus for determining the topography or optical properties of a moving surface of a subject, the apparatus comprising:
    means for acquiring a first image of an area of the subject, on an image-formation area, at a first moment in time while aiming a first type of illumination at the area of the subject and a second image of the area of the subject, on the image-formation area, at a second moment in time while aiming a second type of illumination at the area of the subject;
    means for determining the topography or optical properties of the subject from the first and second images;
    means for acquiring images, on the image-formation area, of a reference area located near to the area of the subject, synchronously with acquiring of the first and second images, in such a way that, in each image of the reference area, illumination of same type is aimed at the reference area; and
    means for using the images created of the reference area to determine the position of image areas corresponding to the area of the subject in the first and second images.

10. The apparatus according to claim 9, wherein the image-formation area is a single unified imaging cell.

11. The apparatus according to claim 9, wherein the image-formation area is formed of a cell structure formed of several separate cameras.

12. The apparatus according to claim 9, wherein the first and second images are acquired of the image areas corresponding to the area of the subject, by illuminating structural illumination patterns of different types in substantially the same direction, and the images are acquired of the reference area by illuminating with no structural illumination pattern in substantially the same direction.

13. The apparatus according to claim 9, wherein the first and second images are acquired of the image areas corresponding to the area of the subject by illuminating light of essentially the same colour in different directions, and the images are acquired of the reference area by illuminating light of essentially the same colour in substantially the same direction.

14. The apparatus according to claim 9, wherein the first and second images are acquired of the image areas corresponding to the area of the subject are by illuminating light that is polarized in substantially differing ways, and the images are acquired of the reference area by illuminating light that is polarized in substantially the same way.

15. The apparatus according to claim 9, wherein the first and second images are acquired of the image areas corresponding to the area of the subject are by illuminating light of spectrally different types, and the images are acquired of the reference area by illuminating light of spectrally the same type.

16. The apparatus according to claim 9, wherein, the first and second images are acquired of the image areas corresponding to the area of the subject by illuminating sine-form illumination patterns in a different phase in substantially the same direction, and the images are acquired of the reference area by illuminating with no structural illumination pattern.

* * * * *